(12) United States Patent
Brandt et al.

(10) Patent No.: US 7,115,254 B1
(45) Date of Patent: Oct. 3, 2006

(54) PERSONAL CARE COMPOSITIONS CONTAINING N,N-DIALLYLDIALKYLAMMONIUM HALIDE/N-VINYLPYRROLIDONE POLYMERS

(75) Inventors: Loralei Marie Brandt, St. Charles, IL (US); Jeffrey Robert Cramm, Batavia, IL (US)

(73) Assignee: Nalco Company, Naperville, IL (US)

( * ) Notice: Subject to any disclaimer, the term of this patent is extended or adjusted under 35 U.S.C. 154(b) by 532 days.

(21) Appl. No.: 10/280,518

(22) Filed: Oct. 25, 2002

(51) Int. Cl.
*A61Q 5/00* (2006.01)
*A61Q 3/00* (2006.01)
*A61Q 19/00* (2006.01)

(52) U.S. Cl. .................. 424/70.11; 424/61; 424/70.1; 424/70.2; 424/401

(58) Field of Classification Search .............. None
See application file for complete search history.

(56) References Cited

U.S. PATENT DOCUMENTS

| | | | |
|---|---|---|---|
| 4,675,178 A | 6/1987 | Klein et al. | |
| 4,710,374 A | 12/1987 | Grollier et al. | |
| 4,764,365 A | 8/1988 | Boothe et al. | |
| 4,772,462 A | 9/1988 | Boothe et al. | |
| 4,842,849 A | 6/1989 | Grollier et al. | |
| 5,627,151 A * | 5/1997 | Detering et al. | 510/475 |

FOREIGN PATENT DOCUMENTS

| | | |
|---|---|---|
| EP | 0 308 189 B1 | 4/1994 |
| EP | 0 308 190 B1 | 4/1994 |

OTHER PUBLICATIONS

Robert Y. Lochhead, PhD., "The History Of Polymers In Hair Care (1940-Present)", Cosmetics & Toiletries, Polymers & Thickeners, Allured Publishing Corp., vol. 103, pp. 23-60, Dec. 1988.

* cited by examiner

*Primary Examiner*—Jyothsna Venkat
(74) *Attorney, Agent, or Firm*—Thomas M. Breininger

(57) ABSTRACT

A cosmetically acceptable composition comprising about 0.01 to about 40 weight percent, based on polymer solids, of a stable solution of a cationic copolymer composed of about 1 to about 99 mole percent diallyl-N,N-disubstituted ammonium halide and about 99 to about 1 mole percent N-vinylpyrollidone, wherein the solution as a RSV of about 0.4 to about 10 dL/g, methods of preparing the composition and methods of using the composition to treat keratinous substrates such as hair, skin and nails.

10 Claims, No Drawings

PERSONAL CARE COMPOSITIONS CONTAINING N,N-DIALLYLDIALKYLAMMONIUM HALIDE/N-VINYLPYRROLIDONE POLYMERS

TECHNICAL FIELD

This invention relates to novel compositions for use in personal care formulations and applications. More particularly, this invention relates to cosmetic compositions comprising N,N-dialkylammonium halide/N-vinylpyrrolidone polymers, to methods of preparing the compositions and to methods of using the compositions to treat keratinous substrates such as hair, skin and nails.

BACKGROUND OF THE INVENTION

The surface properties of human hair, skin and nails are of basic interest in cosmetic science, and there has thus been a long-standing desire to discover cosmetic compositions which will beneficially affect the topical and bulk condition of these keratinous substrates. Such compositions should have adequate adherent properties, so that they are not only absorbed initially, but are also retained on exposure to water. This ability to be absorbed onto the substrate and to resist water rinse off is referred to as substantivity.

Compositions for treating hair should improve the wet and dry combability of the hair, facilitate detangling in wet hair combing and reduce static flyaway in dry hair combing while also imparting softness and suppleness to the hair. Ingredients used in shampoos should impart improved foam stability to the shampoo while hair fixative compositions should impart properties such as good curl retention without having a deleterious effect on wet combability.

With respect to compositions for treating skin, compositions are desired which will function to improve such properties as retention of skin moisture, softening of the skin, attraction of air moisture, retardation of skin water loss, feel and reduction of skin irritations caused by contact with detergents, soaps and the like. Compositions for treating nails should strengthen or harden fragile or brittle nails and improve the overall appearance of the nails.

It is an object of this invention to provide hair styling compositions, particularly aqueous, alcoholic, or hydroalcoholic-based hair setting compositions containing hair setting agents that provide improved hair feel and hold performance.

It is a further object of this invention to provide hair styling compositions, as described above, that provide both improved hair feel and improved holding of the hair for specific ranges of setting agent in the composition.

It is a further object of this invention to provide hair-conditioning compositions, such as shampoos, leave-on or rinse-off conditioners, and especially compositions containing agents that provide improved hair feel and wet combability.

It is a further object of this invention to provide skin compositions, and especially compositions containing agents that improve the condition of the skin through film formation, protection and humectancy.

SUMMARY OF THE INVENTION

This invention is a cosmetically acceptable composition for treating hair, skin and nails comprising about 0.01 to about 40 weight percent, based on polymer solids, of a stable solution of a cationic copolymer composed of about 1 to about 99 mole percent diallyl-N,N-disubstituted ammonium halide and about 99 to about 1 mole percent N-vinylpyrrolidone, wherein the solution as a RSV of about 0.4 to about 10 dL/g.

Cosmetic compositions comprising the polymer of this invention may be utilized in hair, skin and nail conditioning compositions to add luster, slipperiness, enhance feel and form films on the substrate.

Furthermore, unlike traditional polymer resins, the resultant film does not need to be modified by ancillary ingredients such as plasticizers to maintain softness and control without tackiness and without creating a brittle film (less flaking) on the hair.

In addition, the excellent wet combability exhibited by hair care compositions containing the polymer aids in conditioning the hair.

DETAILED DESCRIPTION OF THE INVENTION

The following abbreviations shall have the following meanings.

"DADMAC": diallyldimethylammonium chloride; "PVP": polyvinyl pyrrolidone; "AA": acrylic acid; "MEA": monoethanolamide; "DEA": diethanolamide; "PCA": percarboxlic acid; "USP": United States Pharmacopia; "PVM/MA": polymethyl vinyl ether/Maleic anhydride; "NF": National Formulary; "PABA": p-amino benzoic acid; "AMP": amino methyl propane; "VA": vinyl acetate; "EDTA": ethylenediamine tetracetic acid.

"Diallyl-N,N-disubstituted ammonium halide means monomer of formula $$(H_2C{=}CHCH_2)_2N^+R_1R_2X^-$$

wherein $R_1$ and $R_2$ are independently $C_1$–$C_{20}$ alkyl, aryl or arylalkyl and X is a halogen. A preferred diallyl-N,N-disubstituted ammonium halide is diallyldimethylammonium chloride.

"RSV" stands for Reduced Specific Viscosity. Within a series of polymer homologs which are substantially linear and well solvated, "reduced specific viscosity (RSV)" measurements for dilute polymer solutions are an indication of polymer chain length and average molecular weight according to Paul J. Flory, in *"Principles of Polymer Chemistry"*, Cornell University Press, Ithaca, N.Y., © 1953, Chapter VII, *"Determination of Molecular Weights"*, pp. 266–316. The RSV is measured at a given polymer concentration and temperature and calculated as follows:

$$RSV = \frac{[(\eta/\eta_o) - 1]}{c}$$

$\eta$ = viscosity of polymer solution $\eta_o$ = viscosity of solvent at the same temperature $c$ = concentration of polymer in solution.

The units of concentration "c" are (grams/100 ml or g/deciliter). Therefore, the units of RSV are dl/g. In this patent application, a 1.0 molar sodium nitrate solution is used for measuring RSV. The polymer concentration in this solvent is measured at about 1.0 g/dL. The RSV is measured at 30° C. The viscosities $\eta$ and $\eta_o$ are measured using a Cannon Ubbelohde semimicro dilution viscometer, size 75. The viscometer is mounted in a perfectly vertical position in a constant temperature bath adjusted to 30±0.02° C. When two polymer homologs within a series have similar RSV's that is an indication that they have similar molecular weights.

The cosmetically acceptable composition of this invention comprises about 0.01 to about 40 weight percent, based on polymer solids, of a stable solution of a cationic copolymer composed of about 1 to about 99 mole percent diallyl-N,N-disubstituted ammonium halide and about 99 to about 1 mole percent N-vinylpyrollidone, wherein the solution as a RSV of about 0.4 to about 10 dL/g.

In a preferred aspect of this invention, the diallyl-N,N-disubstituted ammonium halide is diallyldimethylammonium chloride.

In another preferred aspect, the cosmetically acceptable composition comprises about 0.01 to about 20 weight percent, based on polymer solids, of a stable solution of a cationic copolymer composed of about 1 to about 99 mole percent diallyldimethylammonium chloride and about 99 to about 1 mole percent N-vinylpyrollidone.

In another preferred aspect, the cosmetically acceptable composition comprises about 0.01 to about 10 weight percent, based on polymer solids, of a stable solution of a cationic copolymer composed of about 1 to about 99 mole percent diallyldimethylammonium chloride and about 99 to about 1 mole percent N-vinylpyrollidone.

In another preferred aspect, the cosmetically acceptable composition comprises about 0.01 to about 40 weight percent, based on polymer solids, of a stable solution of a cationic copolymer composed of about 1 to about 30 mole percent diallyldimethylammonium chloride and about 99 to about 70 mole percent N-vinylpyrollidone.

In another preferred aspect, the cosmetically acceptable composition comprises about 0.01 to about 40 weight percent, based on polymer solids, of a stable solution of a cationic copolymer composed of about 1 to about 10 mole percent diallyldimethylammonium chloride and about 99 to about 90 mole percent N-vinylpyrollidone.

In addition to the diallyl-N,N-disubstituted ammonium halide/N-vinylpyrollidone polymer, the cosmetically acceptable composition of this invention may include surface-active agents. Surface active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of about 12 to about 16 carbon atoms and an average degree of ethoxylation of about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinanrate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, trlethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric surface-active agents which may be used in the cosmetically acceptable composition of this invention include derivatives of aliphatic secondary and tertiary amines, in which the aliphatic substituent contains about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL™ as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Quaternary ammonium compounds can also be used in the cosmetically acceptable composition of this invention as long as they are compatible in the compositions of the invention, wherein the structure is provided in the CTFA Cosmetic Ingredient Handbook, Fifth Edition, 1988, page 40. Cationic surface-active agents generally include, but are not limited to fatty quaternary ammonium compounds containing about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: behentrimonium chloride, cocotrimonium chloride, cethethyldimonium bromide, dibehenyldimonium chloride, dihydrogenated tallow benzylmonium chloride, disoyadimonium chloride, ditallowdimonium chloride, hydroxycetyl hydroxyethyl dimonium chloride, hydroxyethyl behenamidopropyl dimonium chloride, hydroxyethyl cetyldimonium chloride, hydroxyethyl tallowdimonium chloride, myristalkonium chloride, PEG-2 oleamonium chloride, PEG-5 stearmonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41–42, incorporated herein by reference.

The cosmetically acceptable compositions may include di-long chain amines about $C_{10}$ to $C_{22}$, long chain fatty amines about $C_{10}$ to $C_{22}$, and mixtures thereof. Specific examples include dipalmitylamine, lauramidopropyldimethyl, stearamidopropyl dimethylamine. The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range about 1 to about 8 weight percent, more preferably about 2 to about 6 weight percent. The fatty alcohols may also be ethoxylated. Specific examples include ceteareth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in the cosmetically acceptable composition of this invention include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

The anionic, cationic, nonionic, amphoteric or zwitterionic surface-active agents used in the cosmetically acceptable composition of this invention are typically used in an amount about 0.1 to 50 percent by weight, preferably about 0.5 to about 40 percent by weight, more preferably about 1 to about 20 percent by weight.

The cosmetically acceptable composition of this invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of about 0.5 to about 40 percent by weight, preferably about 0.5 to about 20 percent by weight and more preferably about 0.5 to about 12 percent by weight.

The cosmetically acceptable composition of this invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, synthetic beeswax and the like may be blended together. Alkylmethyl siloxanes with varying degrees of substitution can be used to increase water retained by the skin. Siloxanes such as stearyl dimethicone, known as 2503 Wax, C30–45 alkyl methicone, known as AMS-C30 wax, and stearoxytrimethylsilane (and) stearyl alcohol, known as 580 Wax, each available from Dow Corning®, Midland, Mich., USA. Additonal alkyl and phenyl silicones may be employed to enhance moisturizing properties. Resins such as dimethicone (and) trimethylsoiloxysilicate, known as Dow Corning® 593 or Cyclomethicone (and) Trimethylsiloxysilicate, known as Dow Corning® 749 fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, $C_{12}$ to $C_{16}$ fatty alcohol lactate, isopropyl lanolate, 2-ethylhexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of this invention may also include silicone compounds. Preferably, the viscosity of the silicone component at a temperature of 25° C. is about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane endblocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions of this invention may include volatile and non-volatile silicone oils or fluids. The silicone compounds can be either linear or cyclic polydimethylsiloxanes with a viscosity of about 0.5 to about 100 centistokes. The most preferred linear polydimethylsiloxane compounds have a range of about 0.5 to about 50 centistokes. One example of a linear, low molecular weight, volatile polydimethylsiloxane is octamethyltrisiloxane, available under the tradename Dow Corning® 200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions of this invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity of about 2.0 to about 7.0 centistokes, and mixtures thereof. Preferred cyclomethicones are available from Dow Corning, Midland, Mich., USA under the tradenames Dow Corning® 244 fluid, Dow Corning® 245 fluid, Dow Corning®246, Dow Corning® 344 fluid and Dow Corning® 345 fluid, and Silicone SF-1173 and Silicone SF-1202 from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols, Dow Corning® 3225C and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol, known as Dow Corning® 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munich, Germany. When used, the silicone surfactants are preferably included in the formulations of this invention at a concentration of 0.1 to 30 weight percent, more preferably 1 to 15 weight percent.

Amine functional silicones and emulsions may be utilized in the present invention. Preferred examples include Dow Corning® 8220, Dow Corning® 939, Dow Corning® 949, Dow Corning® 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions of this invention may include volatile hydrocarbon oils. The volatile hydrocarbon comprises from about $C_6$ to $C_{22}$ atoms. A preferred volatile hydrocarbon is an aliphatic hydrocarbon having a chain length of about $C_6$ to $C_{16}$ carbon atoms. An example of such compound includes isohexadecane, under the tradename Permethyl 101A, available from Presperse, South Plainfield, N.J., USA. Another example of a preferred volatile hydrocarbon is $C_{12}$ to $C_{14}$ isoparaffin, under the tradename Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions of this invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17$^{th}$ Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquatemium-10, Guar hydroxypropyltrimonium chloride, Starch hydroxypropyltrimonium chloride, Polyquaternium-4, Polyquatemium-5, Polyquatemium-6, Polyquaternium-7, Polyquatemium-14, Polyquatemium-15, Polyquatemium-22, Polyquatemium-24, Polyquatemium-28, Polyquaternium-32, Polyquatemium-33, Polyquatemium-36, Polyquatemium-37, Polyquatemium-39, Polyquatemium-45, Polyquatemium-47, Polyquatemium-53, Polyquaternium-55 and polymethacrylamidopropyltrimonium chloride, and mixtures thereof. When used, the conditioning polymers are preferably included in the cosmetically acceptable composition of this invention at a concentration of about 0.1 to 10 weight percent, preferably about 0.2 to about 6 weight percent and most preferably about 0.2 to about 5 weight percent.

The cosmetically acceptable composition of this invention may include one or more rheological modifiers. The rheological modifiers which can be used in this invention include, but are not limited to high molecular weight crosslinked homopolymers of acrylic acid, and acrylates/$C_{10-30}$ alkyl acrylate crosspolymer, such as the Carbopol® and Pemulen® series, both available from Noveon, Inc, Cleveland, Ohio, USA; anionic acrylate polymers such as Salcare® AST and cationic acrylate polymers such as Salcare® SC96, available from Ciba Specialties, High Point, N.C., USA; acrylamidopropylttrimonium chloride/acrylamide; hydroxyethyl methacrylates polymers, Steareth-10 Allyl Ether/Acrylate Copolymer; Acrylates/Beheneth-25 Metacrylate Copolymer, known as Aculyn® 28, available from International Specialties, Wayne, N.J., USA; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of about 0.01 to about 12 weight percent, preferably about 0.05 to about 10 weight percent and most preferably about 0.1 to about 6 weight percent.

The cosmetically acceptable composition of this invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The antioxidants will be present at about 0.01 to about 5 weight percent, preferably about 0.1 to about 3 weight percent and most preferably about 0.2 to about 2 weight percent of the cosmetically acceptable composition.

The cosmetically acceptable composition of this invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis (hydroxypropyl) aminobenzoate, 2-ethylhexy 1-2-cyano-3,3-diphenylacrylate, homomenthyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and typically is about 0.1 to about 10 percent by weight, preferably about 2 to about 8 percent by weight.

The cosmetically acceptable composition of this invention may include one or more preservatives. Example of preservatives, which may be used include, but are not limited to 1,2-dibromo-2,4-dicyano butane (Methyldibromo Glutaronitrile, known as MERGUARD®, ONDEO Nalco Chemical Company, Naperville, Ill., USA), benzyl alcohol, imidazolidinyl urea, 1,3-bis-(hydroxymethyl)-5,5-dimethyl-2,3-imidazolidinedione (e.g., DMDM Hydantoin, known as GLYDANT®, Lonza, Fairlawn, N.J., USA.), methylchloroisothiazolinone and methylisothiazolinone (e.g., Kathon®, Rohm & Haas Co., Philadelphia, Pa., USA), methyl paraben, propyl paraben, phenoxyethanol, and sodium benzoate, and mixtures thereof.

The cosmetically acceptable composition of this invention may include any other ingredient normally used in cosmetics. Examples of such ingredients include, but are not limited to buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the unsaturated quaternary ammonium compounds described herein and then used in the cosmetically acceptable composition of this invention. The treated pigments are then more effective as sunscreen actives and for use in color cosmetics such as make up and mascara.

The cosmetically acceptable composition of this invention can be presented in various forms. Examples of such forms include, but are not limited a solution, liquid, cream, emulsion, dispersion, gel, thickening lotion.

The cosmetically acceptable composition of this invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerine, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70 percent by weight, for example about 0.1 to about 70 percent by weight, relative to the weight of the total composition.

The cosmetically acceptable composition of this invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The cosmetically acceptable composition of this invention also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

In a preferred aspect of this invention, the cosmetically acceptable composition further comprises one or more excipients selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines of about $C_{10}$ to $C_{22}$, long chain fatty amines of about $C_{10}$ to $C_{22}$, fatty alcohols, ethoxylated fatty alcohols and di-tail phospholipids.

In another preferred aspect, the cosmetically acceptable composition is selected from the group consisting of shampoos, aftershaves, sunscreens, lotions, hand and body creams, liquid soaps, bar soaps, bath oil bars, shaving creams, dishwashing liquids, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

Compositions for treating skin include leave-on or rinse-off skin care products such as lotions, hand/body creams, shaving gels or shaving creams, body washes, sunscreens, liquid soaps, deodorants, anti-perspirants, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

The skin care compositions of this invention may be prepared as either oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, the humectant, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

The condition and appearance of the hair can be improved by applying a composition that conditions or softens the hair and/or helps maintain the hair in a particular style or shape. Different vehicles have been utilized for setting the hair including lotions, gels, mousses, waxes, creams, balms, styling sprays and hair sprays. These compositions are all formulated with polymeric resins as the traditional materials to impart curl retention and stiffness. In "The History of Polymers in Haircare," Cosmetics and Toiletries, Volume 103, December 1988, R. Y. Lochhead discusses many synthetic polymers that have been used in creating styling aids.

The general principles relative to the hair styling and setting are discussed in detail by Zviak, in The Science of Hair Care, Marcel Dekker, pp. 149–181 (1986) and by Dallal and Rochafort in Hair and Hair Care, Marcel Dekker, pp. 105–165 (1997). Zviak and Dallal and Rocafort review polymers used in hair styling products and the formulation principles used to produce a hair styling composition that provides such beneficial hair setting properties as curl retention, wet combing, body, bounce, stylability and control. In the formulation of any end-use hair styling product, examples show that some of these benefits must be sacrificed to some degree to achieve a competing benefit (such as good hold with smooth feel). Therefore, the formulation of hair styling compositions is often a compromise, striking the right balance of both hold and feel properties.

Compositions for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

Hair care compositions of this invention give slippery feel and that can be easily rinsed from the hair due to the presence of the polymer, volatile silicones, other polymers, surfactants or other compounds that may alter the deposition of materials upon the hair.

In the case of cleansing formulations such as a shampoo for washing the hair, or a liquid hand soap, or shower gel for washing the skin, the compositions contain anionic, cationic, nonionic, zwitterionic or amphoteric surface-active agents typically in an amount about 3 to about 50 percent by weight, preferably about 3 to about 20 percent, and their pH is general in the range about 3 to about 10 percent.

Preferred shampoos of this invention contain combinations of anionic surfactants with zwitterionic surfactants and/or amphoteric surfactants. Especially preferred shampoos contain 0 to about 16 percent active of alkyl sulfates, 0 to about 50 weight percent of ethoxylated alkyl sulfates, and 0 to about 50 weight percent of surface-active agents selected from the nonionic, amphoteric, and zwitterionic surface-active agents, with at least 5 weight percent of either alkyl sulfate, ethoxylated alkyl sulfate, or a mixture thereof, and a total surfactant level of about 10 weight to about 25 percent.

The shampoo for washing hair also can contain other conditioning additives such as silicones and conditioning polymers typically used in shampoos. U.S. Pat. No. 5,573,709 provides a list of non-volatile silicone conditioning agents that can be used in shampoos. The conditioning polymers for use with the present invention are listed in the Cosmetic, Toiletries and Fragrance Associations (CTFA) dictionary. Specific examples include the Polyquaterniums (example Polyquaternium-1 to Polyquaternium-50), Guar Hydroxypropyl Trimonium Chloride, Starch Hydroxypropyl Trimonium Chloride and Polymethacrylamidopropyl Trimonium Chloride.

Other preferred compositions are used in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially resins, acrylic acid thickeners available from B.F. Goodrich; xanthan gums; sodium alginates; gum arabic; cellulose derivatives and poly(ethylene oxide) based thickeners, and it is also possible to achieve thickening by means of a mixture of polyethylene glycol stearate or distearate or by means of a mixture of a phosphoric acid ester and an amide. The concentration of thickener is generally about 0.05 to about 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition may also contain one or more additional hair fixative polymers. When present, the additional hair fixative polymers are present in a total amount of about 0.25 to about 10 percent by weight. Any additional hair fixative resin(s) can be selected from the following group, as long as the resin is compatible with a given polymer of the present invention. This group consists of: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/Maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/Methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/Methacrylic acid copolymer, PVP/hexadecene copolymer, PVP/VA copolymer, PVP/vinyl acetate/itaconic acid copolymer, shellac, sodium acrylate/vinyl alcohol copolymer, sodium carrageenan, starch diethylaminoethyl ether, stearylvinyl ether/Maleic anhydride copolymer, sucrose benzoate/sucrose acetate isobutyrate/butyl benzyl phthalate copolymer, sucrose benzoate/sucrose acetate isobutyrate/butyl benzyl phthalate/Methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/Methacryloxybenzophenone-1 copolymer, vinyl acetate/crotonic acid/vinyl neodecanoate copolymer, and mixtures thereof. In "The History of Polymers in Haircare," Cosmetics and Toiletries, Volume 103, December 1988, R. Y. Lochhead discusses many synthetic polymers that have been used in creating styling aids and is incorporated herein by reference.

The hair styling compositions of this invention are applied to wet or dry hair by spraying or by rubbing onto the hair manually. The treated hair is then mechanically fixed in the desired configuration using, for example, any of a variety of rollers or curlers. In the case of application to wet hair, the hair is then dried using ambient air, electric or hot air drying using, for example, a blow dryer. The hair is then combed to provide the desired hairstyle.

Saccharides may be used to thicken, enhance aesthetics and provide extra conditioning, feel or curl retention benefits or other formulation benefits. Saccharides which may be used in the present invention include nonionic or cationic saccharides such as agarose, amylopectins, amyloses, arabinans, arabinogalactans, arabinoxylens, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitins, chitins, chitosan, chitosan pyrrolidone carboxylate, chitosan glycolate chitosan lactate, cocodimonium hydroxypropyl oxyethyl cellulose, colominic acid (poly(N acetyl-neuraminic acid)), corn starch, curdlan, dermatin sulfate, dextrans, furcellarans, dextrans, cross-linked dextrans, dextrin, emulsan, ethyl hydroxyethyl cellulose, flaxseed saccharide (acidic), galactoglucomannans, galactomannans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquatemium-4, polyquaternium-10, polyquaternium-28, potato starch, protopectins, psyllium seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer *Encyclopedia of Chemical Technology*, Fourth Edition, Vol. 16, John Wiley and Sons, NY pp. 578–611 (1994) which is incorporated entirely by reference. Complex carbohydrates found in Kirk-Othmer *Encyclopedia of Chemical Technology*, Fourth Edition, Vol. 4, John Wiley and Sons, NY pp. 930–948, 1995 which is incorporated herein by reference.

The foregoing may be better understood by reference to the following Examples, which are presented for purposes of illustration and are not intended to limit the scope of this invention.

EXAMPLE 1

Preparation of 70 Mole Percent diallyldimethylammonium chloride/30 Mole Percent N-vinylpyrrolidone Copolymer.

Deionized water (7.4 g), 63.6% diallyldimethylammonium chloride (364.4 g), ethylenediamine tetraacetic acid (0.19 g), and N-vinylpyrrolidone (68.3 g) are mixed in a 1.5 liter cylindrical reaction flask. The reactor is equipped with a helical mixer, heating mantle, RTD temperature sensor, nitrogen purge line, and condenser. The pH is adjusted to 7–8 with sulfuric acid. The monomer solution is purged with nitrogen and heated to 60° C. An initiator solution is prepared by dissolving 2,2'-azobis(2-amidinopropane) dihydrochloride (5.4 g) in deionized water (30.6 g). A portion of the initiator solution (2 g) is added to the reactor. After 0.5 hour a slow feed (2.5 g/hour) of initiator solution is started and the temperature is maintained at 60° C. After 3.5 hour, deionized water (~50 g) is added to the viscous polymer solution to improve mixing. The reaction mixture is then heated to 80° C. while continuing the initiator feed. When the temperature reaches 80° C. the initiator flow rate is increased to 12 g/hour. After 1 hour, deionized water (~50 g) is added to the viscous polymer solution to improve mixing. After another hour, the initiator solution feed is finished and the polymer solution is mixed at 80° C. for an additional 2 hours. The polymer is diluted to ~23% with hot deionized water (~730 g). Preservatives are added and the solution is stirred at 85° C. for an additional hour.

EXAMPLE 2

Preparation of 2 Mole Percent diallyldimethylammonium chloride/98 Mole Percent N-vinylpyrrolidone Copolymer.

Deionized water (413.6 g), 64.3% diallyldimethylammonium chloride (8.07 g), ethylenediamine tetraacetic acid (0.19 g) and N-vinylpyrrolidone (174.8 g) are mixed in a 1.5 liter cylindrical reaction flask. The reactor is equipped with a helical mixer, heating mantle, RTD temperature sensor, nitrogen purge line, and condenser. 4,4'-Azobis(4-cyanopentanoic acid) (2.4 g) is added with stirring. The monomer solution is neutralized to pH 7 with 25% aqueous NaOH (2.3 g). The solution is purged with nitrogen and heated at 50° C. for 19 hours. Deionized water (~100 g) is added to the viscous polymer solution to improve mixing and the polymer is heated to 85° C. This temperature is maintained for 1 hour, at which point the polymer is diluted to 15.5% with hot deionized water (~450 g). Preservatives are added and the solution is stirred at 85° C. for an additional hour.

Representative polymers prepared according to the method of Examples 1 and 2 suitable for use in preparing the cosmetically acceptable compositions of this invention are listed in Table 1. In Table 1, Polymers A–F and J–L are available from ONDEO Nalco Company, Naperville, Ill. Polymers G, H and I are commercially available reference polymers.

TABLE 1

Representative Polymers

|  | Composition (Mole %) | Percent Polymer actives | RSV[4] (dL/g) |
|---|---|---|---|
| Polymer A | 10% DADMAC/90% VP | 25% | 1.7 |
| Polymer B | 30% DADMAC/70% VP | 25% | 1.3 |
| Polymer C | 50% DADMAC/50% VP | 25% | 0.85 |
| Polymer D | 70% DADMAC/30% VP | 23% | 1.2 |
| Polymer E | 90% DADMAC/10% VP | 25% | 1.1 |
| Polymer F | 95% DADMAC/5% VP | 20% | 1.1 |
| Polymer G[1] | Polyvinyl pyrrolidone | 100% | NA |
| Polymer H[2] | Polyvinyl pyrrolidone/vinyl acetate | 100% | NA |
| Polymer I[3] | PolyDADMAC | 40% | NA |
| Polymer J | 2% DADMAC/98% VP | 15.4% | 2.2[5] |
| Polymer K | 1% DADMAC/99% VP | 15.3% | 2.9[5] |
| Polymer L | 5% DADMAC/95% VP | 25.2% | 1.9 |

[1,2]Polyvinyl pyrrolidone (PVP K-30) and Polyvinylpyrrolidone/Vinyl acetate (PVP/VA S-630), International Specialties, Wayne, NJ, USA.
[3]Merquat ® 100, ONDEO Nalco, Naperville, IL, USA.
[4]Measured at 1.00% polymer in 1N NaNO$_3$.
[5]Measured at 0.10% polymer in 1N NaCl.

EXAMPLE 2

Shampoo Formulations.

Shampoo formulations prepared using representative polymers of this invention and reference polymers are shown in Table 2.

TABLE 2

Shampoo Formulations Containing Representative and Reference Polymers

| | Formulation | | | | | | |
|---|---|---|---|---|---|---|---|
| | I % w/w | II % w/w | III % w/w | IV % w/w | V % w/w | VI % w/w | VII % w/w |
| Water, Deionized | QS | QS | QS | QS | QS | QS | QS |
| Disodium Laureth-3 Sulfosuccinate[1] | 3.00 | 3.00 | 3.00 | 3.00 | 3.00 | 3.00 | 3.00 |
| Ammonium Lauryl Sulfate[2], 30% | 30.00 | 30.00 | 30.00 | 0.00 | 0.00 | 0.00 | 0.00 |
| Sodium Laureth Ether Sulfate[3], 30% | 0.00 | 0.00 | 0.00 | 30.00 | 30.00 | 30.00 | 30.00 |
| Coco-glucoside[4] | 3.00 | 3.00 | 3.00 | 3.00 | 3.00 | 3.00 | 3.00 |
| PEG-120 Methyl Glucose Dioleate[5] | 2.10 | 2.10 | 2.10 | 2.10 | 2.10 | 2.10 | 2.10 |
| Coco Betaine[6] | 8.00 | 8.00 | 8.00 | 5.33 | 5.33 | 5.33 | 5.33 |
| Methyl Paraben[7] | 0.20 | 0.20 | 0.20 | 0.20 | 0.20 | 0.20 | 0.20 |
| Propyl Paraben[8] | 0.10 | 0.10 | 0.10 | 0.10 | 0.10 | 0.10 | 0.10 |

TABLE 2-continued

Shampoo Formulations Containing Representative and Reference Polymers

| | I % w/w | II % w/w | III % w/w | IV % w/w | V % w/w | VI % w/w | VII % w/w |
|---|---|---|---|---|---|---|---|
| Sodium Chloride | 0.15 | 0.15 | 0.15 | 0.00 | 0.00 | 0.00 | 0.00 |
| Propylene Glycol | 0.00 | 0.00 | 0.00 | 0.50 | 0.50 | 0.50 | 0.50 |
| Polymer A | 0.00 | 2.20 | 0.00 | 2.20 | 0.00 | 0.00 | 0.00 |
| Polymer B | 0.00 | 0.00 | 0.00 | 0.00 | 2.20 | 0.00 | 0.00 |
| Polymer C | 0.00 | 0.00 | 0.00 | 0.00 | 0.00 | 2.20 | 0.00 |
| Polymer G | 0.00 | 0.00 | 0.55 | 0.00 | 0.00 | 0.00 | 0.00 |
| Propylene Glycol | 0.00 | 0.00 | 0.00 | qs | qs | qs | qs |
| Citric Acid, 50%[9] | qs | qs | qs | qs | qs | qs | qs |
| Visual Observation | Clear | Clear | Hazy | Clear | Clear | Hazy | Clear |

[1]Geropon SBFA-30, Rhone-Poulenc, Cranbury, NJ, USA.
[2]Standapol A, Cognis Corporation, Hobokin, NJ, USA.
[3]Steol CS 230, Stepan, Northfield, IL, USA.
[4]Plantaren 818UP, Cognis Corporation, Hobokin, NJ, USA.
[5]Glucamate ® DOE-120, Amerchol Corporation, Edison, NJ, USA.
[6]Velvetex AB45, Cognis Corporation, Hobokin, NJ, USA.
[7]Nipagin ®, NIPA Inc., Wilmington, DE, USA.
[8]Nipasol ®, NIPA Inc., Wilmington, DE, USA.
[9]EM Science, Gibbstown, NJ, USA.

EXAMPLE 3

Shampoo Viscosity.

The viscosity of the shampoo formulations prepared in Example 2 are measured on a Brookfield RV-DV I+ using spindle 5 at speed 20 for 60 seconds at approximately 23.5° C. The results are summarized in Table 3.

TABLE 3

Viscosity of Shampoo Formulations Prepared using Representative Polymers of this Invention and Reference Polymers

| Formulation | Composition | Viscosity (cps) |
|---|---|---|
| I | No polymer | 4090 |
| II | 2.20% weight Polymer A | 4830 |
| III | 0.55% weight Polymer G | 2890 |
| IV | 2.20% weight Polymer A | 6800 |
| V | 2.20% weight Polymer B | 6940 |
| VI | No polymer | 7500 |

As shown in Table 3, shampoo examples can be formulated with representative polymers at acceptable viscosities above at least 3000 cps.

EXAMPLE 4

Table 4. Film Formation of Representative Polymers

The film formation properties of aqueous solutions of representative polymers is measured by plating ten grams of a 1% polymer solution onto a petri dish and drying for 16 hours at 23° C. and 30% Relative humidity. The film is characterized in Table 4.

TABLE 4

Film Formation with Representative Polymers at 1% Weight Polymer Solids*

| Composition | Film characterization |
|---|---|
| 4.0% weight Polymer A | Clear, hard and glossy |
| 4.0% weight Polymer B | Clear, hard and glossy |
| 4.33% weight Polymer C | Clear, hard and glossy |
| 4.0% weight Polymer D | Clear, hard and glossy |
| 4.3% weight Polymer E | Clear, hard and glossy; harder than A–D |
| 4.0% weight Polymer F | Clear, hard and glossy; harder than A–D |
| 1.0% weight Polymer G | Clear and glossy but more easily scratched |

*Refer to Table 1 for polymer actives.

As shown in Table 4, representative polymers of this invention can form a clear glossy film that is less brittle and less easily etched than comparative polymer G.

EXAMPLE 5

Ease of Combing.

Ease of Combing (leave on) is assessed using 1% weight polymer solids at pH 6.0 using the wet combing Diastron procedure described below. A Diastron Mini-Tensile Tester, model MTT 160 is utilized for wet combing evaluation. The results are summarized in Table 5.

1. Five two-gram bleached blonde tresses obtained from DeMeo Brothers are cut to six inches and pre-washed in 5% active Sodium Lauryl Ether Sulfate.
2. Tress baseline combing is taken by tangling hair one time between combing runs.
3. Tresses are soaked for three minutes in a 1% active polymer solution adjusted to pH 6.0.
4. Approximately one gram of solution is allowed to remain on the hair.
5. Tresses are combed five times per run and results are averaged. A percent improvement is calculated.

TABLE 5

Wet Combing Improvement of Representative Polymers - Leave-on Treatment

| Composition | % Improvement |
| --- | --- |
| Water Control | 00.00 |
| Polymer A | 84.62 |
| Polymer C | 50.96 |
| Polymer E | 55.62 |
| Polymer G | 30.10 |
| Polymer H | 17.38 |

As shown in Table 5, the wet combing of the polymers A, C and E when used in a leave-on fashion on the hair is superior to the water control. Polymer A combs significantly better than comparative polymers G and H.

EXAMPLE 6

Wet Combability Panel Test.

The wet combability of hair treated with solutions of representative polymers (pH 6.0) is assessed as described below. The results are summarized in Table 6.
1. Prepare a 1-gram sample, six inches in length each of virgin hair (International Hair Importers, Bellerose, N.Y., USA).
2. Apply 1 gram of polymer onto tress. Tresses are stroked 25 times to ensure coverage.
3. Comb each tress with the wide end of the Sally styling comb to detangle.
4. Randomized panelists comb the hair tresses and rate tresses according to intensity (1=no drag, easy to comb to 5=drag and pull, very hard to comb).

TABLE 6

Wet Combing of Representative Polymers - Leave-on Treatment

| Composition | Panelist rating, avg. (n = 4) |
| --- | --- |
| Water Control | 4.0 |
| 1% solids Polymer I | 3.6 |
| 1% solids Polymer H | 3.6 |
| 1% solids Polymer E | 2.4 |
| 1% solids Polymer A | 2.3 |
| 1% solids Polymer C | 1.8 |
| 1% solids Polymer G | 3.7 |

As shown in Table 6, wet combability is improved relative to the water control in all examples. Wet combability is improved to the greatest extent by polymers A, C and E.

EXAMPLE 7

Leave-on or Rinse-Off Conditioner Formulations.

Conditioner formulations prepared with or without a representative polymer of this invention and reference polymers are shown in Table 7.

TABLE 7

Conditioner Formulation Containing a Representative Polymer

| Formulation | VII<br>% w/w | VIII<br>% w/w |
| --- | --- | --- |
| Water, Deionized | qs | qs |
| Hydroxyethyl Cellulose | 0.2 | 0.2 |
| Stearyl Alcohol | 2.5 | 2.5 |
| Cetyl Alcohol | 3.5 | 3.5 |
| Dicetyldimonium chloride | 2.0 | 2.0 |
| Polymer A (active basis) | 0 | 0.25 |
| Cyclomethicone | 1.0 | 1.0 |

The conditioner formulations in Table 7 are made by methods known or similar to those known by one skilled in the art. The conditioner with representative polymer A (Formulation VIII) improves the wet and dry feel of the hair tresses after one usage.

EXAMPLE 8

Panel Test of Slippery Feel of Conditioner Formulations.

Slippery feel can aid the aesthetics of a product and allow hair fibers to slide past one another. This is an important goal of any conditioning product. A panel evaluated the slippery and smooth feel of the formulations of Table 7 using the following protocol. The results are tabulated in Table 8.
1. Prepare a 1-gram sample, six inches in length each of virgin hair (International Hair Importers, Bellerose, N.Y., USA).
2. Apply one gram of polymer onto tresses. Tresses are stroked 25 times to ensure coverage.
3. Comb each tress with the wide end of the Sally styling comb to detangle.
4. Randomized panelists run their fingers from top to bottom of the hair tresses and rate tresses according to intensity (1 not slippery, drag to 5=very slippery).

TABLE 8

Panel Assessment of Leave-on Conditioner

| Formulation | Slippery Feel (n = 4) |
| --- | --- |
| Water | 1.3 |
| VII | 3.5 |
| VIII | 4.6 |

As shown in Table 8, the polymers of this invention can be added to conditioner to enhance the slipperiness of the product.

EXAMPLE 9

Panel Test of Stiffness and Flaking of Representative Polymers

Stiffness is often a signal to the consumer that the polymer is helping to hold the hair in place. A stiffness panel is used to evaluate the stiffness or rigidity of the hair with the representative polymers (1.0 weight percent, pH 6.0) using the following protocol. The results are summarized in Table 9.
1. Prepare a 1-gram sample, six inches in length each of virgin hair (International Hair Importers, Bellerose, N.Y., USA).
2. Apply 1 gram of polymer onto tress. Tresses are stroked 25 times to ensure coverage.

3. Detangle each tress with the wide end of the Sally styling comb.
4. Dry tresses at 30% relative humidity and 23° C.
5. Randomized panelists feel the stiffness and rate tresses according to intensity on a continuous scale (1=not stiff through 5=very stiff). Panelists also rate the flaking and dusting after combing through the hair tresses.

TABLE 9

Stiffness and Flaking Panel Assessment of Polymer

| Composition | Stiffness (n = 4) | Flaking (n = 4) |
|---|---|---|
| Water | 1.0 | No |
| Polymer A | 3.9 | No |
| Polymer B | 3.1 | No |
| Polymer C | 3.4 | No |
| Polymer D | 3.7 | No |
| Polymer E | 3.8 | No |
| Polymer G | 3.0 | No |
| Polymer H | 2.5 | No |

As shown in Table 9, representative polymers of this invention impart stiffness to hair with no flaking or dusting observed.

EXAMPLE 10

Curl Retention.

Curl retention of representative polymers at 1% polymer actives and pH 6.0 is measured using the following protocol. The results are summarized in Table 10.

1. Prepare 5 replicates for each polymer to be tested and three samples for the control.
2. Soak tresses such that approximately 0.5 gram of 1% active polymer remains on each tress.
3. Comb each tress to detangle with the wide end of the Sally styling comb.
4. Clip the hair onto a clamp that is mounted on the hair-combing stand.
5. Equilibrate tresses in a controlled humidity chamber set at 50% relative humidity and 25° C. overnight.
6. Adjust chamber humidity to between 85 and 90 percent by placing 500 grams of deionized water/170 gram sodium sulfite in a glass 8×10 baking dish.
7. Wind the curls in a helical configuration.
8. Record the initial lengths of all the tresses at t=0 (Initial Length=Lo).
9. Place the curls in the humidity chamber and set the timer for 15 minutes.
10. Measure the length (Lt) of each tress (from the bottom of the clamp to the bottom of the curl) every 15 minutes for 2 hours. Note: Start subsequent timings every time measurement of the first tress is taken.
11. Calculate curl retention using the following formula:

% Curl Retention=$(L-Lt)/(L-Lo) \times 100$

Where L=length of tress, Lt=Length of tress at time t, Lo=length of tress at time t=0

Note: Higher % curl retention indicates better performance.

TABLE 10

Curl Retention of Representative Polymers

| Composition | Curl Retention % at t = 0.25 hrs. | Curl Retention % at t = 2 hrs. |
|---|---|---|
| Polymer A (Test 1) | 95.8 | 61.2 |
| Polymer G (Test 1) | 79.0 | 37.3 |
| Polymer L (Test 2) | 89.3 | 65.0 |
| Polymer G (Test 2) | 80.9 | 44.9 |

As shown in Table 10, the curl retention of Polymers A and L is superior to that of comparative polymer G.

EXAMPLE 11

Curl Memory.

The curl memory of hair treated with representative polymers of this invention is measured as follows. The results are summarized in Table 11.

1. Comb 2-gram, 6-inch length washed hair tresses ten times to detangle using Sally comb (large tooth part).
2. Apply 1.0 gram of polymer solution to each hair tress.
3. Allow hair tresses to dry for two hours in 30% Relative Humidity at 23° C.
4. Curl each tress for 30 seconds using Conair Instant Heat curling iron (one-inch barrel size at setting 20).
5. Release the curl and allow to cool in a 25° C. and 50% relative humidity room. The initial length is recorded.
6. Record the fall-out length after 10 minutes, 30 minutes.
7. Calculate the curl memory using the following formula:

% Curl Retention=$(L-Lt)/(L-Lo) \times 100$

Where L=length of tress, Lt=Length of tress at time t, Lo=length of tress at time t=0

Higher percentages indicate better curl memory.

TABLE 11

Curl Memory for Representative Polymers

| Composition (1.0 weight percent polymer, pH = 6) | % Curl Memory 10 minutes | % Curl Memory 30 minutes |
|---|---|---|
| Water Control | 57.4 | 46.7 |
| Polymer A | 72.9 | 63.2 |
| Polymer B | 72.6 | 64.3 |
| Polymer G | 67.1 | 55.5 |
| Polymer H | 78.7 | 66.2 |

As shown in Table 11, the curl memory of hair treated with representative polymers is improved over that of the water control.

EXAMPLE 12

Styling Cream.

Styling cream formulations prepared with or without a representative polymer of this invention and reference polymers are shown in Table 12.

TABLE 12

Styling Creams containing Representative Polymers

| Composition | IX Weight % w/w | X Weight % w/w |
|---|---|---|
| Water, Deionized | qs | qs |
| Polyquaternium-37/Propylene glycol/Dicaprylate Dicaprate and PPG-1 Trideceth-6[1], 50% | 4.00 | 4.00 |
| Polymer A | 1.00 | 0.00 |
| Polyvinypyrollidone[2] | 0.00 | 0.25 |
| Cyclopentasiloxane[3] | 1.00 | 1.00 |

[1]Salcare® SC96, Ciba Specialty Chemicals, Highpoint, NC, USA.
[2]PVP-K30, International Specialties Products, Wayne, NJ, USA.
[3]Dow Corning® 245 fluid, Dow Corning, Midland, MI, USA.

EXAMPLE 13

Wet Combability Panel Test of Styling Creme Formulations.

The wet combability of hair treated with compositions IX and X is measured using the panel test described in Example 6. The results are summarized in Table 13.

TABLE 13

Panel Wet Combing of Styling Cream with Representative Polymer

| Composition | Wet Combing (n = 4) |
|---|---|
| Water Control | 3.4 |
| IX | 1.8 |
| X | 1.7 |

As shown in Table 13, a styling cream formulation containing a representative polymer of this invention (composition IX) combs better than the untreated water control and similarly to that of a styling cream formulation containing a comparative polymer.

EXAMPLE 14

Skin Care Compositions.

Polymers of this invention can also be utilized for treating the skin. Without being bound by theory, polymers of this invention may form a protective film on the skin or nails. Skin care lotion formulations are shown in Table 14.

TABLE 14

Skin Care Lotions containing Representative Polymers

| Composition | XI % w/w | XII % w/w | XIII % w/w |
|---|---|---|---|
| Water, Deionized | qs | qs | qs |
| Hydroxypropyl methyl cellulose[1] | 0.25 | 0.25 | 0.25 |
| Glycerol[2] | 2.00 | 2.00 | 2.00 |
| Disodium EDTA[3] | 0.05 | 0.05 | 0.05 |
| Triethanolamine, 99% | 0.42 | 0.42 | 0.42 |
| Crosslinked acrylic acid[4] | 0.1 | 0.1 | 0.1 |
| Petrolatum[5] | 5.00 | 5.00 | 5.00 |
| Mineral oil[6] | 3.00 | 3.00 | 3.00 |
| Ethylene Glycol Monostearate[7] | 2.00 | 2.00 | 2.00 |
| Paraffin Wax[8] | 1.00 | 1.00 | 1.00 |
| Beeswax | 1.00 | 1.00 | 1.00 |
| Dimethicone[9] | 0.5 | 0.5 | 0.5 |
| Acrylates/C10–30 Alkyl Acrylate[10] | 0.05 | 0.05 | 0.05 |
| Methyldibromo glutaronitrile (and) propylene glycol[12] | 0.20 | 0.20 | 0.20 |
| Polymer A | 0.00 | 1.00 | 0.00 |
| Polymer G | 0.00 | 0.00 | 1.00 |

[1]Hydroxypropyl methylcellulose, Methocel® 40-100, Dow Chemical, Midland, MI, USA.
[2]Glycerine, EM Science, Gibbstown, NJ, USA.
[3]Disodium EDTA, Dissolvine Na2X, Akzo Nobel, Chicago, IL, USA.
[4]Carbomer, Carbopol® 980, Goodrich, Akron, OH, USA.
[5]Penreco® Snow White Petrolatum, Karns City, PA, USA.
[6]Blandol, Witco, USA.
[7]EGMS VA Proprietary ester, Goldschmidt, Hopewell, VA, USA.
[8]SP192P, Strahl & Pitch, West Babylon, NY, USA.
[9]Dow Corning® 200 fluid, 100 Cs, Dow Corning, Midland, MI, USA.
[10]Pemulen® TR-2 Polymeric Emusifier, Goodrich, Akron, OH, USA.
[11]SP922P, Strahl & Pitch, West Babylon, NY, USA.
[12]Merguard® 1105, ONDEO Nalco, Naperville, IL, USA.

EXAMPLE 15

Skin Feel Attributes of Skin Care Formulations Containing Representative Polymers.

The skin lotions of Table 14 are qualitatively assessed for skin feel attributes. Approximately 0.05 ml of lotion sample is spread onto forearm and massaged into the skin in a circular fashion. Appearance (shine), rub-in, after-feel and delayed afterfeel are assessed by panelists. The results are shown in Table 15.

TABLE 15

Qualitative Assessment of Representative Polymers

| Composition | Appearance | Rub-in | After-feel | Delayed Afterfeel (5 minutes) |
|---|---|---|---|---|
| XI | Healthy, slight shine, moisturizing | Short rub-in time | Tacky, then smooth | Soft and smooth |
| XII | Healthy, slight shine, moisturizing | Longest time to rub-in | Little sticky then smooth; slight drag | Soft and smooth |
| XIII | Healthy, slight shine, moisturizing | Medium rub-in | Smooth; slight tacky; slight drag | Soft, slight dry feeling; some drag |

As shown in Table 15, composition XIII containing a representative polymer of this invention is well liked in comparison to the control (no polymer) and Example XII containing a comparative polymer.

EXAMPLE 16

Rinse Off Combing Sensory Results

The wet combability of hair treated with solutions of representative polymers (0.5 weight percent polymer solids, pH 6) is assessed as described below. The results are summarized in Table 16.

1. Prepare a 1-gram sample, six inches in length each of virgin hair (International Hair Importers, Bellerose, N.Y., USA).
2. Apply 1 gram of polymer onto tress. Stroke tresses 25 times to ensure coverage.
3. Comb each tress with the wide end of the Sally styling comb to detangle.

4. Rinse tresses under 38° C. tap water for 15 seconds and blot.
5. Randomized panelists comb the hair tresses and rate tresses according to intensity (1=no drag, easy to comb to 5=drag and pull, very hard to comb).

TABLE 16

Wet Combing of Representative Polymers - Rinse-off Treatment

| Composition | Panelist rating, avg. (n = 4) |
|---|---|
| Water Control | 2.7 |
| 0.5% % solids Polymer L | 1.5 |
| 0.5% solids Polymer I | 3.4 |
| 0.5% solids Polymer G | 2.8 |

As shown in Table 16, wet combability is improved to the greatest extent by polymer L.

EXAMPLE 17

Rinse Off Combing, Diastron Results.

Hair tresses are prepared according to a modification of the leave-on Diastron combing methodology utilizing 0.5% active polymer and rinsing polymer from the hair tresses prior to combing. The results are summarized in Table 17.

TABLE 17

Diastron Wet Combing of Representative Polymers - Rinse-off Treatment

| Composition | Average Percent Improvement % |
|---|---|
| 0.5% solids Polymer L | 97.1 |
| 0.5% solids Polymer G | −9.00 |

As shown in Table 17, wet combability is improved to the greatest extent by composition containing polymer L.

Although this invention has been described in detail for the purpose of illustration, it is to be understood that such detail is solely for that purpose and that numerous modifications, alterations and changes can be made therein by those skilled in the art without departing from the spirit and scope of the invention except as it may be limited by the claims. All changes which come within the meaning and range of equivalency of the claims are to be embraced within their scope.

We claim:

1. A method of treating hair, skin or nails comprising applying a cosmetically acceptable composition comprising from about 0.01 to about 40 weight percent, based on polymer solids, of a stable solution of a cationic copolymer composed of about 1 to about 99 mole percent diallyl-N,N-disubstituted ammonium halide and about 99 to about 1 mole percent N-vinylpyrollidone, wherein the solution as a RSV of about 0.4 to about 10 dL/g to said hair, skin or nails.

2. The method of claim 1, wherein the cosmetically acceptable composition further comprises one or more excipients selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines of about $C_{10}$ to $C_{22}$, long chain fatty amines of about $C_{10}$ to $C_{22}$, fatty alcohols, ethoxylated fatty alcohols and di-tail phospholipids.

3. The method of claim 1, wherein the cosmetically acceptable composition selected from the group consisting of shampoos, aftershaves, sunscreens, lotions, hand and body creams, liquid soaps, bar soaps, bath oil bars, shaving creams, dishwashing liquids, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

4. The method of claim 1, wherein the diallyl-N,N-disubstituted ammonium halide is diallyldimethylammonium chloride.

5. The method of claim 4, wherein cosmetically acceptable composition comprises about 0.01 to about 20 weight percent, based on polymer solids, of a stable solution of a cationic copolymer composed of about 1 to about 99 mole percent diallyldimethylammonium chloride and about 99 to about 1 mole percent N-vinylpyrollidone.

6. The method of claim 4, wherein cosmetically acceptable composition comprises about 0.01 to about 10 weight percent, based on polymer solids, of a stable solution of a cationic copolymer composed of about 1 to about 99 mole percent diallyldimethylammonium chloride and about 99 to about 1 mole percent N-vinylpyrollidone.

7. The method of claim 4, wherein cosmetically acceptable composition comprises about 0.01 to about 40 weight percent, based on polymer solids, of a stable solution of a cationic copolymer composed of about 1 to about 30 mole percent diallyldimethylammonium chloride and about 99 to about 70 mole percent N-vinylpyrollidone.

8. The method of claim 4, wherein cosmetically acceptable composition comprises about 0.01 to about 40 weight percent, based on polymer solids, of a stable solution of a cationic copolymer composed of about 1 to about 10 mole percent diallyldimethylammonium chloride and about 99 to about 90 mole percent N-vinylpyrollidone.

9. The method of claim 4, wherein cosmetically acceptable composition is selected from the group consisting of shampoos, conditioners, permanent waves, hair relaxers, hair bleaches, hair detangling lotion, styling gel, styling glazes, spray foams, styling creams, styling waxes, styling lotions, mousses, spray gels, pomades, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

10. The method of claim 4, wherein cosmetically acceptable composition is selected from the group consisting of lotions, hand and body creams, shaving gels or shaving creams, body washes, sunscreens, liquid soaps, deodorants, anti-perspirants, suntan lotions, after sun gels, bubble baths, hand or mechanical dishwashing compositions.

* * * * *